United States Patent
Cook et al.

(10) Patent No.: US 9,339,630 B2
(45) Date of Patent: May 17, 2016

(54) RETRACTABLE DRUG DELIVERY SYSTEM AND METHOD

(75) Inventors: Brian Cook, Windsor, CA (US); James Mitchell, Windsor, CA (US); Natividad Vasquez, Windsor, CA (US); Gianfranco Pellegrini, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1443 days.

(21) Appl. No.: 12/389,070

(22) Filed: Feb. 19, 2009

(65) Prior Publication Data

US 2010/0211153 A1 Aug. 19, 2010

(51) Int. Cl.
*A61F 2/95* (2013.01)
*A61M 25/00* (2006.01)
*A61F 2/966* (2013.01)
*A61F 2/91* (2013.01)
*A61M 25/06* (2006.01)

(52) U.S. Cl.
CPC ............ *A61M 25/0082* (2013.01); *A61F 2/966* (2013.01); *A61F 2/91* (2013.01); *A61F 2/95* (2013.01); *A61F 2002/9665* (2013.01); *A61F 2250/0068* (2013.01); *A61M 25/0068* (2013.01); *A61M 2025/0057* (2013.01); *A61M 2025/0681* (2013.01)

(58) Field of Classification Search
CPC .................. A61M 25/0082; A61M 2025/0057; A61F 2/966; A61F 2/91; A61F 2/95; A61F 2250/0068
USPC .................. 606/200; 623/1.11, 1.12, 1.3, 1.46
See application file for complete search history.

(56) References Cited

U.S. PATENT DOCUMENTS

| | | | |
|---|---|---|---|
| 5,776,142 A | 7/1998 | Gunderson | |
| 5,900,246 A | 5/1999 | Lambert | |
| 6,136,006 A | 10/2000 | Johnson et al. | |
| 6,290,710 B1 | 9/2001 | Cryer et al. | |
| 6,340,356 B1 * | 1/2002 | Navia | 604/104 |
| 6,350,278 B1 | 2/2002 | Lenker et al. | |
| 6,398,758 B1 | 6/2002 | Jacobsen et al. | |
| 6,939,361 B1 * | 9/2005 | Kleshinski | 606/200 |
| 2001/0031981 A1 * | 10/2001 | Evans et al. | 606/200 |
| 2002/0054900 A1 | 5/2002 | Kamath et al. | |
| 2004/0054402 A1 | 3/2004 | DiCarlo | |
| 2006/0259119 A1 | 11/2006 | Rucker | |
| 2006/0282149 A1 * | 12/2006 | Kao | 623/1.11 |
| 2007/0100422 A1 * | 5/2007 | Shumer et al. | 623/1.11 |
| 2008/0125848 A1 | 5/2008 | Kusleika et al. | |
| 2008/0312664 A1 * | 12/2008 | Bardsley | 606/142 |

* cited by examiner

*Primary Examiner* — Ryan J Severson
*Assistant Examiner* — Anh Dang

(57) ABSTRACT

A system for treating a vascular condition includes a catheter having an inner member and an outer member, the outer member concentrically arranged about the inner member and a retractable drug delivery device disposed at a distal end of the inner member. A coating disposed on at least a portion of an outer surface of the retractable drug delivery device includes at least one therapeutic agent.

10 Claims, 6 Drawing Sheets

RETRACTABLE DRUG DELIVERY SYSTEM AND METHOD

TECHNICAL FIELD

This invention relates generally to biomedical devices that are used for treating vascular conditions. More specifically, the invention relates to a retractable device for delivering therapeutic agents to a vascular treatment site.

BACKGROUND OF THE INVENTION

Heart disease, specifically coronary artery disease, is a major cause of death, disability, and healthcare expense. Coronary artery disease (CAD) results from arteriosclerosis of blood vessels serving the heart. Arteriosclerosis is a hardening and narrowing of the arteries commonly accompanied by a deposition of a waxy substance. This substance, known as plaque, is made of cholesterol, fatty compounds, calcium, and the blood-clotting material fibrin. Often the arteries of the heart can suddenly become so severely blocked that there is an inadequate blood supply after the blockage, leading to the occurrence of a myocardial infarction or "heart attack." Although some heart attacks are caused by such "hard" plaques, many are caused by "soft" or vulnerable plaques. A vulnerable plaque is an inflamed part of an artery that can burst. This can lead to the formation of a blood clot, which can reduce or block the flow of blood.

Plain-old-balloon-angioplasty (POBA) is an exemplary medical procedure to widen obstructed blood vessels narrowed by plaque deposits. The procedure may be used in coronary or peripheral arteries. In an angioplasty procedure, a catheter having a special inflatable balloon on its distal end is navigated through the patient's arteries and is advanced through the artery to be treated to position the balloon within the narrowed region (stenosis). The region of the stenosis is expanded by inflating the balloon under pressure to forcibly widen the artery. After the artery has been widened, the balloon is deflated and the catheter is removed from the patient.

A significant difficulty associated with balloon angioplasty is that in a considerable number of cases the artery may again become obstructed in the same region where the balloon angioplasty had been performed. The repeat obstruction may be an immediate abrupt closure, which is usually caused by an intimal flap or a segment of plaque or plaque-laden tissue that loosens or breaks free as a result of the damage done to the arterial wall during the balloon angioplasty. More commonly, closure of the artery (restenosis) may occur at a later time, for example two or more months after the angioplasty, for reasons not fully understood and may require repeat balloon angioplasty or bypass surgery. When such longer-term restenosis occurs, it usually is more similar to the original stenosis, that is, it is in the form of cell proliferation and renewed plaque deposition in and on the arterial wall.

To reduce the incidence of re-obstruction and restenosis, several strategies have been developed. Implantable devices, such as stents, have been used to reduce the rate of angioplasty related re-obstruction and restenosis. The stent is placed inside the blood vessel after the angioplasty has been performed. A catheter typically is used to deliver the stent to the arterial site to be treated.

Another strategy for treating the incidence of re-obstruction and restenosis, as well as other vascular problems, includes the use of therapeutic agents or drugs. Therapeutic agents may be delivered locally or systemically. Stents capable of delivering one or more therapeutic agents have been used to treat the damaged vessel and reduce the incidence of deleterious conditions including thrombosis and restenosis. One drawback to the use of a stent for agent delivery is that stent insertion and implantation may cause undesirable reactions such as inflammation, infection, thrombosis, and proliferation of cell growth that occludes the passageway.

One drawback to systemic delivery of therapeutic agents to a vascular treatment site is that the dosage of the required agent to adequately treat the condition may be too high to achieve a therapeutic dose at the treatment site or may be toxic to the patient.

It is an object of this invention, therefore, to provide a device for effective, controlled delivery of therapeutic agents to a treatment site. It is a further object to provide a system and method for treating heart disease and other vascular conditions, that overcome the deficiencies and limitations described above

SUMMARY OF THE INVENTION

One aspect of the present invention provides a system for treating a vascular condition. The system comprises a catheter including an inner member and an outer member, the outer member concentrically arranged about the inner member, and a retractable drug delivery device disposed at a distal end of the inner member. The system further includes a coating disposed on at least a portion of an outer surface of the retractable drug delivery device and at least one therapeutic agent within the coating.

Another aspect of the invention provides a method of treating a vascular condition. The method comprises delivering a retractable drug delivery device including a coating and at least one therapeutic agent to a treatment site via catheter; deploying the retractable drug delivery device at the treatment site; contacting an outer surface of the retractable drug delivery device with a vessel wall at the treatment site; and delivering a therapeutically effective amount of the at least one therapeutic agent to the treatment site as a function of degradation of the coating.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the figures wherein like numbers refer to like structures. The terms "distal" and "proximal" are used herein with reference to the treating clinician during the use of the catheter system; "distal" indicates an apparatus portion distant from, or a direction away from the clinician and "proximal" indicates an apparatus portion near to, or a direction towards the clinician.

Figure 1:
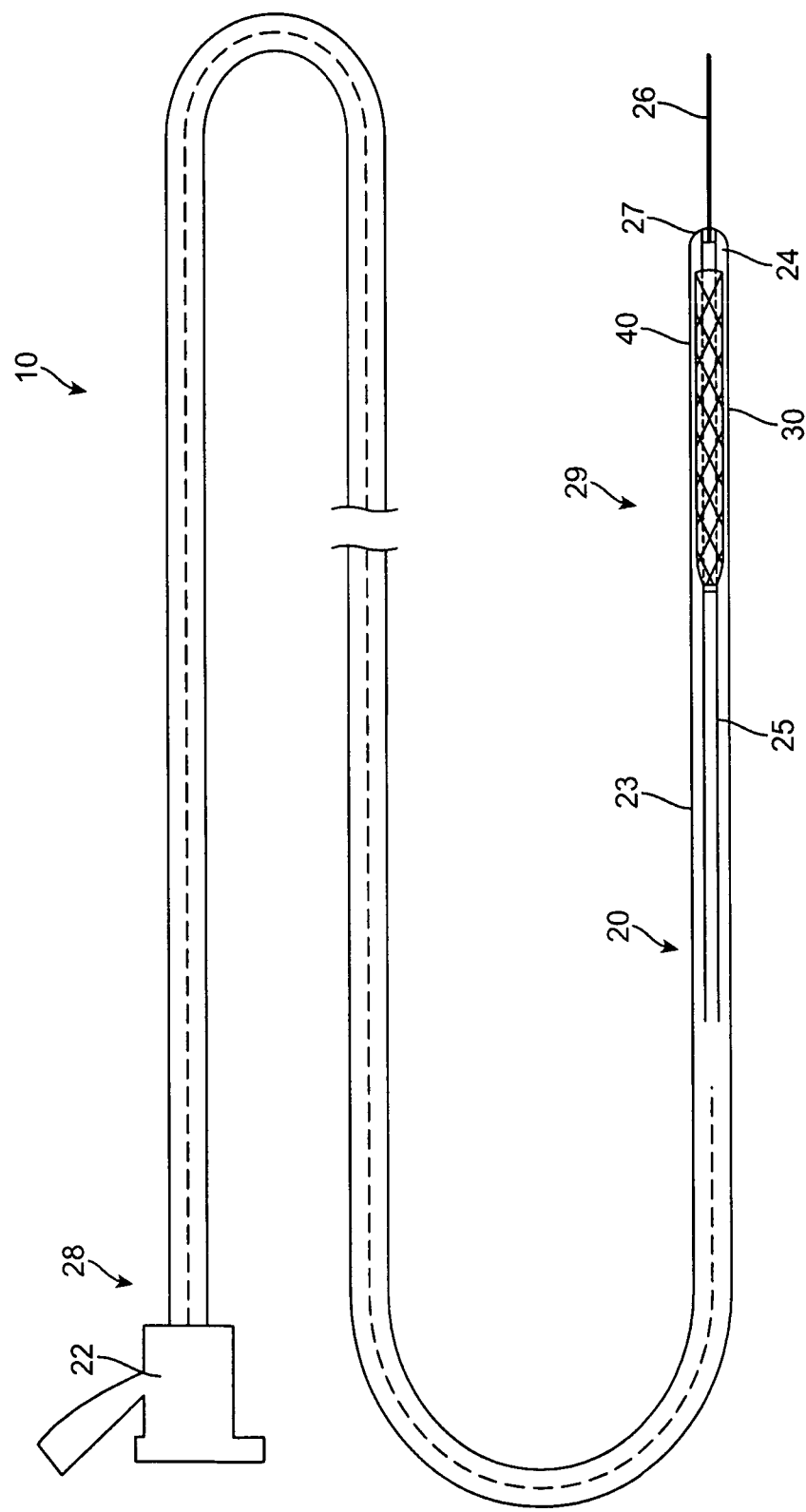
FIG. 1 is a schematic illustration of a system for treating a vascular condition comprising a retractable drug delivery device coupled to a catheter, in accordance with one embodiment of the present invention.
Figure 2:
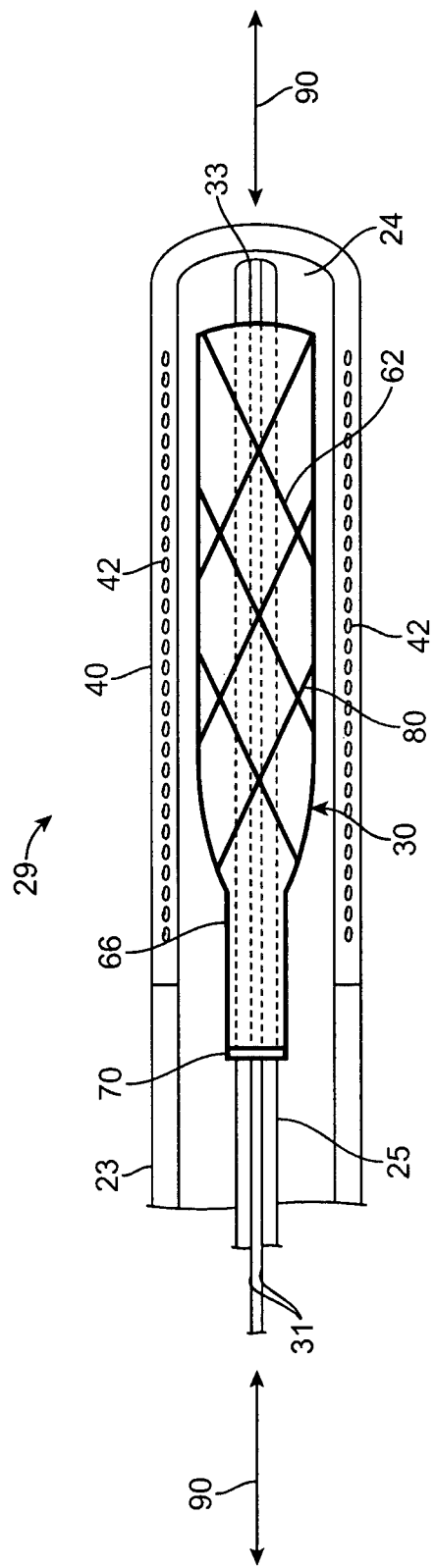
FIG. 2 is a detailed schematic illustration of the retractable drug delivery device of FIG. 1.

Referring to the drawings, FIG. 1 is a perspective view of a therapeutic agent delivery system 10 and FIG. 2 is a detailed view of a distal portion 29 of therapeutic agent delivery system 10, in accordance with one embodiment of the present invention. System 10 includes catheter 20, guidewire 26 and retractable drug delivery device 30. FIGS. 1 and 2 illustrate retractable drug delivery device 30 in a delivery configuration. The term "catheter" as used herein, includes any number of intravascular devices capable of performing the functions according to the invention and are not limited to the examples provided herein.

Catheter 20 comprises an outer member 23 and an inner member 25. Outer member 23 comprises an elongate tubular member disposed around and coaxial with inner member 25. Outer member 23 includes a substantially circular wall including an inner surface that defines lumen 24. In one embodiment, inner member 25 includes a guidewire lumen 31 and a distal aperture 33 formed therethrough allowing catheter 20 to be advanced over pre-positioned guidewire 26.

Outer member 23 and inner member 25 of catheter 20 may be manufactured from material such as, for example, thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, combinations thereof, and the like. Outer member 23 of catheter 20 may also include metallic and or polymeric reinforcement to increase trackability and pushability, as is known in the art.

Catheter 20 is secured at proximal end 28 to a suitable fitting assembly 22. Fitting assembly 22 includes components necessary for the control, placement and actuation of system 10 and the delivery and placement of retractable drug delivery device 30. Catheter 20 may include a distal rounded end 27 to ease travel through the vasculature or other body lumen.

Catheter 20 further includes sheath 40 disposed at distal end 29 of outer member 23. Sheath 40 covers retractable drug delivery device 30 disposed at a distal end of inner member 25. Sheath 40 may be attached to or formed integrally with outer member 23. In one embodiment sheath 40 comprises a retractable sheath that is retracted to deploy retractable drug delivery device 30. In one embodiment, retractable sheath 40 is operably connected to an actuation device of fitting assembly 22. In one embodiment, sheath 40 includes a reinforcing layer 42 to aid in restraining retractable drug delivery device 30 during delivery. The reinforcing layer may be a metallic or polymeric filament or plurality of filaments braided or woven into or within sheath 40. In another embodiment, sheath 40 has a multi-layer construction including a reinforcing layer and at least one polymeric layer. In one embodiment, a reinforcing layer is disposed between two polymeric layers. The reinforcing layer may comprise a braided, coiled, helical or woven metallic or polymeric material suitable for providing a restraining force to the self-expanding retractable drug delivery device 30 during delivery.

In another embodiment, sheath 40 comprises a stationary sheath having a reinforcing layer for restraining retractable drug delivery device 30 during delivery. In this embodiment, retractable drug delivery device 30 is deployed by advancing inner member 25 in a distal direction while maintaining outer member in a stationary position.

Figure 3:
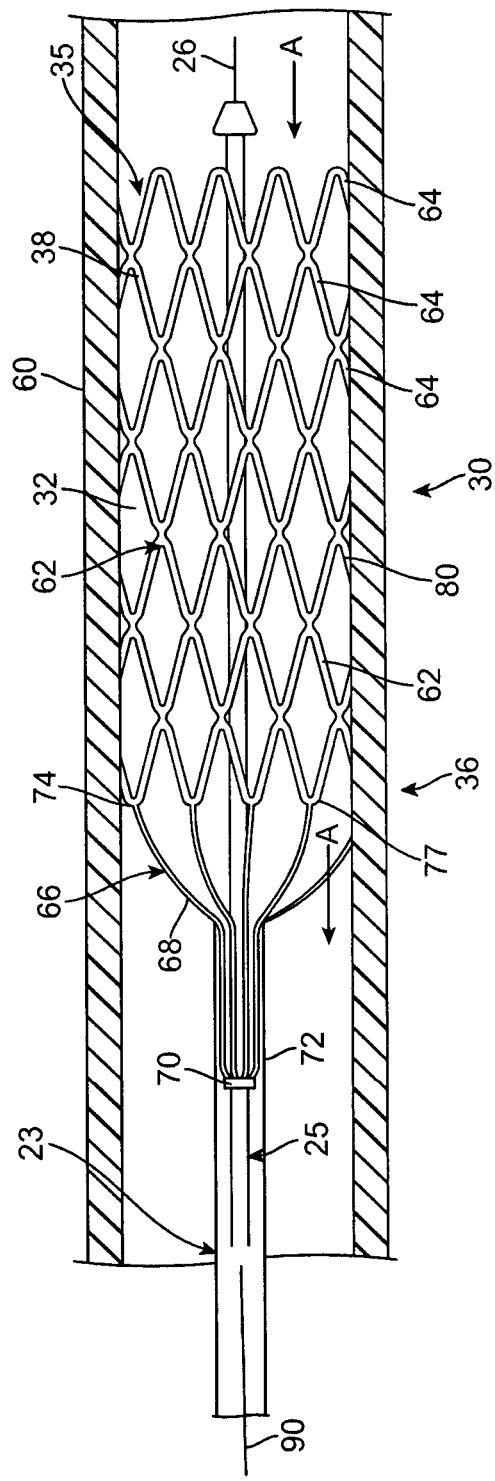
FIG. 3 detailed schematic illustration of the retractable drug delivery device of FIG. 1 deployed within a vessel, in accordance with the present invention.

Referring also to FIG. 3, FIG. 3 illustrates a detailed view of one embodiment of retractable drug delivery device 30 in accordance with the present invention. FIG. 3 shows retractable drug delivery device 30 in a deployed configuration, deployed at a treatment site within vessel 60.

Retractable drug delivery device 30 includes a scaffold body 32, comprising a plurality of scaffold struts 62 and a plurality of transition struts 66, and attachment 70. Scaffold struts 62 and transition struts 66 are manufactured from a skeletal framework of material forming a generally tubular structure capable of self-expanding when deployed from sheath 40. Scaffold body 32 is manufactured from a self-expanding material such as, for example, nickel titanium alloys and/or other alloys that exhibit superlastic behavior (i.e., capable of significant distortion without plastic deformation). Suitable materials for scaffold body 32 include, but are not limited to, nitinol, nickel titanium (ASTM & NiTi alloys comprising but not exclusively limited to Ni+Ti+(Fe, Cr, and/or Cu); Au—Cd alloys; CuZnAl; CuSn; InTi; TiNi; Au; MnCu; and the like, and combinations thereof. Furthermore, the scaffold body 32 material may include any number of other metallic and/or polymeric biocompatible materials recognized in the art for such devices.

Scaffold body 32 defines a passageway 35 extending along a longitudinal axis 90. In one embodiment, scaffold struts 62 include a plurality of identical cylindrical segments 64 placed end to end and arranged successively along the longitudinal axis 90. In one embodiment, the cylindrical segments 64 have a sinusoidal configuration. The scaffold body 32 is formed by shaping a metallic wire or filament, or by laser cutting the stent from a metallic sheet, or any other appropriate method. If needed, the surface of the scaffold body 32 is cleaned by washing with surfactants to remove oils, mechanical polishing, electropolishing, etching with acid or base, or any other effective means to expose a clean, uniform surface that is ready for applying a coating.

In one embodiment, scaffold struts 62 are manufactured from a plurality of filaments or wires arranged in a braided, woven or helical pattern. Those skilled in the art will recognize that the number of segments may vary and that the described retractable drug delivery device 30 is provided merely as an example.

Transition struts 66 comprise an elongated strut having a proximal end 72 connected to attachment 70 and a distal end 74 connected to a proximal end 36 of a scaffold strut 62. Transition struts 66 may be attached to attachment 70 by a weld, adhesive or any other means known in the art. Attachment 70 may comprise a ring or band secured to inner member 25 by welding or an adhesive. In another embodiment, attachment 70 is formed integrally with inner member 25. In one embodiment, attachment 70 comprises a raised portion of inner member 25 including a plurality of openings into which distal ends of transition struts 66 are inserted and secured. Distal end 74 of transition strut 66 may be attached to a distal end of scaffold strut 62 by welding, adhesive or any other means known in the art. In one embodiment, distal end 74 is attached to a crown portion 77 of a cylindrical segment 64.

In another embodiment, scaffold body 32 is manufactured from a single piece of material. In one embodiment, scaffold body 32 is cut from a tubular piece of material. In another embodiment, scaffold body 32 is cut from a sheet of material that is then formed into a tubular structure.

Figure 4:
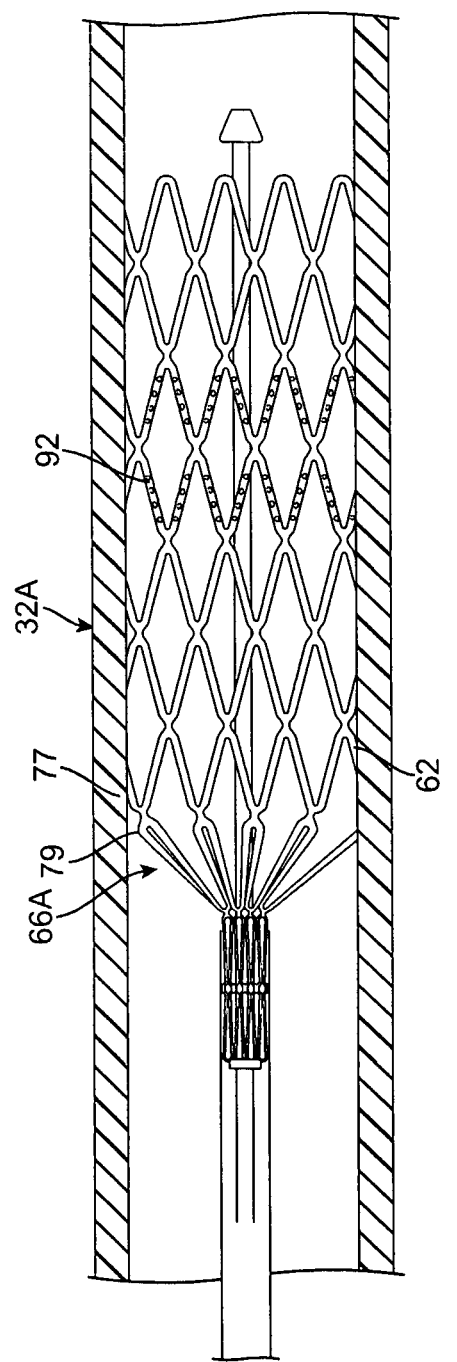
FIG. 4 is a detailed schematic illustration of another embodiment of a retractable drug delivery device, in accordance with the present invention.

As shown in FIG. 3, transition struts 66 may be a single elongated strut. In one embodiment, transition strut 66 includes an arcuate portion 68. Arcuate portion 68 is configured to provide an easier retraction of the scaffold body upon completion of the drug delivery. Those with skill in the art will appreciate that the transition struts may take other forms and configurations. FIG. 4 illustrates another embodiment of a scaffold body 32A having transition struts 66A. In this embodiment, transition struts 66A comprises a sinusoidal strut having a plurality of crown portions 79 connected to corresponding crown portions 77 of scaffold struts 62. In another embodiment, scaffold body 32 is manufactured from a plurality of continuous filaments braided to form the scaffold struts and the transition struts.

In FIG. 3, retractable drug delivery device 30 is shown in an expanded state in which the cylindrical segments 64 have been expanded radially outward from the longitudinal axis 90. Retractable drug delivery device 30 may be compressed into a smaller diameter (i.e., when loaded within a catheter lumen, as seen in FIG. 1) for delivery within a vessel lumen, at which point retractable drug delivery device 30 may be expanded to deliver at least one therapeutic agent to a vessel wall. When deployed at the treatment site and in the expanded configuration, passageway 35 of scaffold 32 is formed to allow blood flow indicated by arrows A. The open passageway 35 allows for longer dwell time of device 30 at a treatment site as compared to a device that would block the blood flow. The increased dwell time provides a clinician the time to ensure that a therapeutically effective dose of therapeutic agent or drug is transferred to the treatment site.

Retractable drug delivery device 30 includes a therapeutic agent coating 80. Therapeutic agent coating 80 includes at least one therapeutic agent disposed on at least a portion of an outer surface 38 of scaffold struts 62. In one embodiment, at least a portion of the outer surface 38 of scaffold struts 62 include a plurality of recessed drug reservoirs 92 (FIG. 4). These drug reservoirs provide an increased drug loading capability to retractable drug delivery device 30. The drug reservoirs may take the form of pores, pits, and channels of various sizes and shapes and may be configured to suit a particular strut configuration and drug delivery application.

During deployment of retractable drug delivery device 30, a therapeutically effective amount of the at least one therapeutic agent is released at the treatment site.

The at least one therapeutic substance or drug may comprise a biologically or pharmacologically active substance. In one embodiment, the biologically or pharmacologically active substance may be suspended in a polymer matrix or carrier to prevent premature elution of the active therapeutic substance. In one embodiment, the polymer matrix or carrier is biodegradable or bioresorbable such that it is absorbed in the body. The polymer matrix may comprise biodegradable polymers such as polylactic acid (PLA), polyglycolic acid, and their copolymers, polyethylene oxide (PEO), caproic acid, polyethylene glycol, polyanhydrides, polyacetates, polycaprolactones, poly(orthoesters), polyamides, polyurethanes and other suitable polymers.

The term "biologically or pharmacologically active substance" refers to any substance, whether synthetic or natural, that has a pharmacological, chemical, or biological effect on the body or a portion thereof. Suitable biologically or pharmacologically active materials that can be used in embodiments of the present invention include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, fibrinolytics, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine, doxazosin, and sirolimus or other—limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Recombinant DNA products, or other bioactive agents, diagnostic agents, radioactive isotopes, or radiopaque substances may be used depending on the anticipated needs of the targeted patient population. Such genes or nucleic acids can first be packaged in liposomes or nanoparticles. Furthermore, collagen-synthesis inhibitors, such as tranilast, may be used.

The formulation containing the therapeutic agent may additionally contain excipients including solvents or other solubilizers, stabilizers, suspending agents, antioxidants, and preservatives, as needed to deliver an effective dose of the therapeutic agent to the treatment site. The coating 80 containing therapeutic agent may be applied to the surface 38 of scaffold struts 62 by any means known in the art such as, for example, by spraying, dipping and vapor deposition. In one embodiment of the invention, the coating is applied as a liquid by dipping or spraying, and then dried to remove solvent using air, vacuum, or heat, and any other effective means of causing the formulation to adhere to the stent framework. In one embodiment, a cap coat is applied over therapeutic coating 80 to prevent or reduce damage to coating 80 during storage, insertion and delivery of the retractable drug delivery device 30 to a treatment site.

Figure 5:
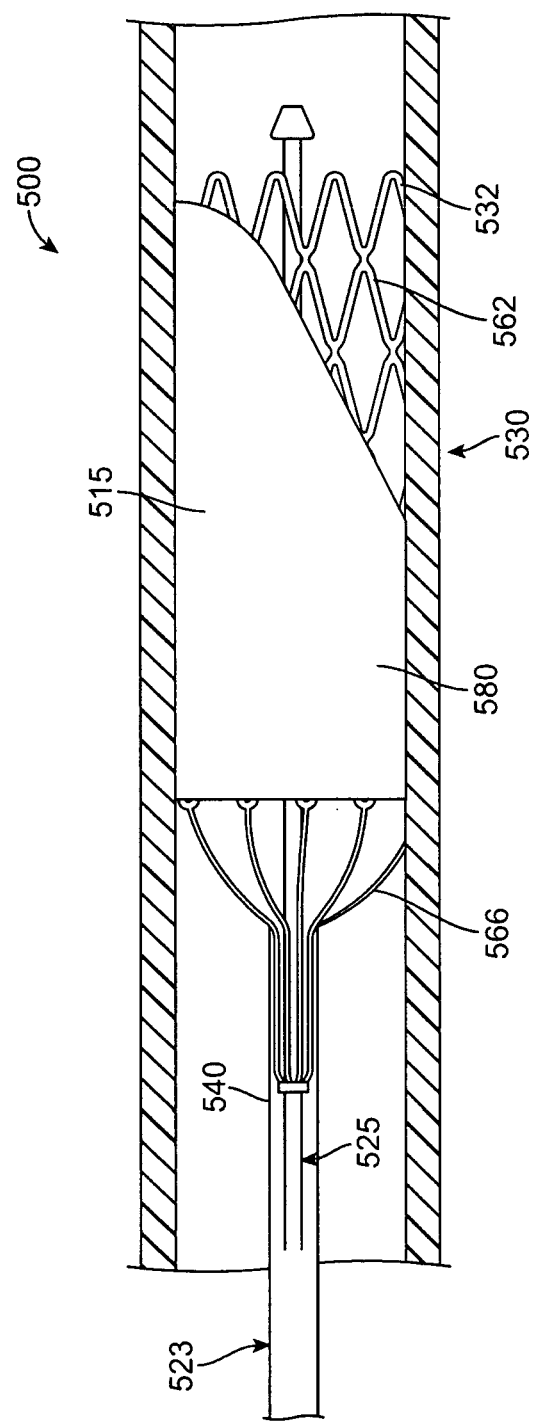
FIG. 5. is a detailed schematic illustration of another embodiment of a retractable drug delivery device, in accordance with the present invention.

FIG. 5 illustrates another embodiment of a system 500 for treating a vascular condition in accordance with the present invention. System 500 is the same as or similar to system 10 described above. Components in common with system 10 will not be described further. System 500 includes a retractable drug delivery device 530 operably attached to inner member 525. Retractable drug delivery device 530 includes scaffold body 532 including scaffold struts 562 and transition struts 566. Scaffold body 532 is the same as or similar to scaffold body 32 described above. In this embodiment, retractable drug delivery device 530 further includes membrane 515 disposed over and attached to scaffold struts 562. Membrane 515 may be attached to scaffold struts by sutures, adhesive or any other means known to one with ordinary skill in the art. Membrane 515 comprises a thin sheet of biocompatible synthetic or natural material. In other embodiments, membrane 515 may be a woven or braided material. Membrane 515 may be made of: biodegradable polymers such as polylactic acid (PLA), polyglycolic acid, and their copolymers, polyethylene oxide (PEO), caproic acid, polyethylene glycol, polyanhydrides, polyacetates, polycaprolactones, poly(orthoesters), polyamides, polyurethanes and other suitable polymers; polymers such as polyesters, fluorinated polymers, polyethylene terephthalate (PET), expanded polytetrafluoroethylene (ePTFE), and the like; polyester fabrics, e.g., polyethylene terephthalate (PET), Dacron, ultra high molecular weight polyesters, and the like; and/or bioabsorbable sheets, e.g., poly(D,L-lactide), poly(L-lactide), and other suitable polymer sheets.

In this embodiment, membrane 515 includes a therapeutic coating 580 disposed on an outer surface. The therapeutic coating is the same as or similar to coating 80 described above. Coating 580 may be uniformly disposed on membrane 515 or may be disposed on portions of membrane 515 as required for a particular application. In the expanded configuration at a treatment site, the coated outer surface of membrane 515 contacts a vessel wall and transfers a therapeutic dose of drug or agent to the treatment site.

Figure 6:
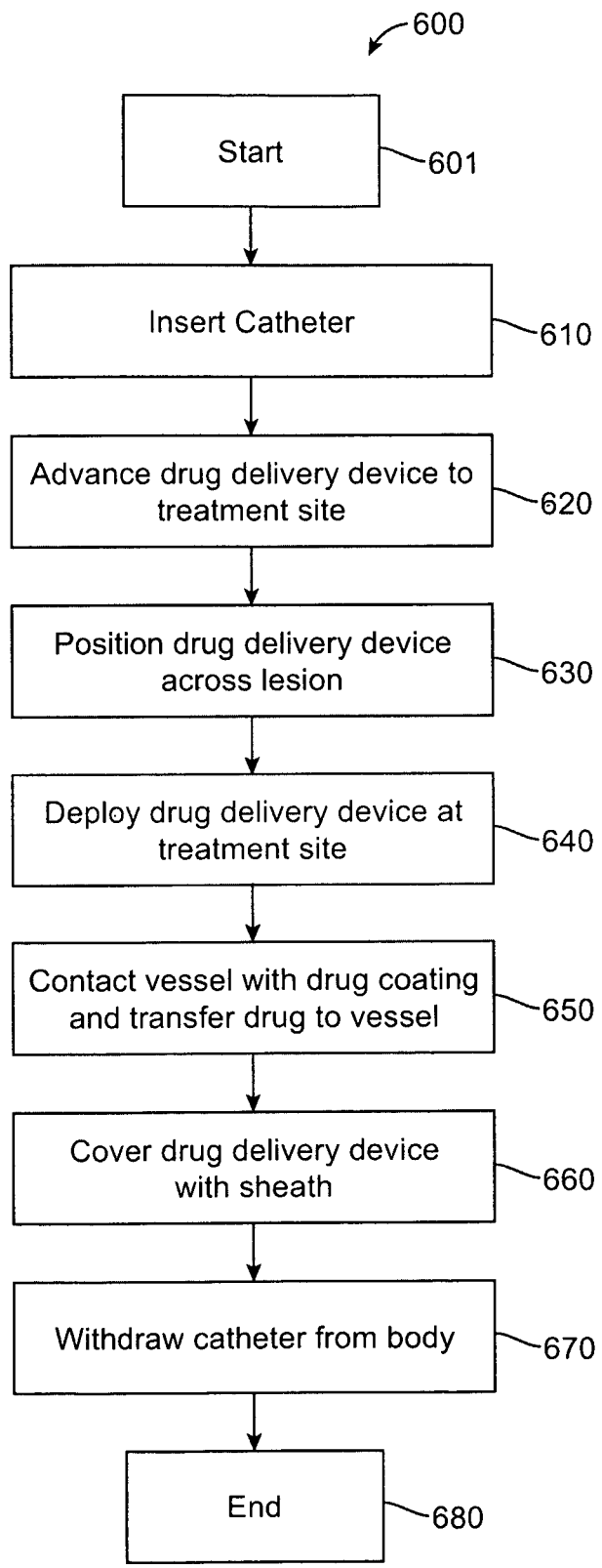
FIG. 6 is a flow diagram of a method for treating a vascular condition, in accordance with the present invention

FIG. 6 is a flowchart of method 600 for treating a vascular condition using a retractable drug delivery device, in accordance with the present invention. Method 600 begins at 601. At Block 610 a catheter including a retractable drug delivery device 30 is inserted into a vascular lumen. The retractable drug delivery device 30 includes a coating having at least one therapeutic agent as described above. Those with skill in the art will recognize that the retractable drug delivery device may be used to treat conditions throughout the vascular system as well as other lumens throughout a body such as a ureter and urethra.

Next, at Block 620, a distal end of catheter 20 is advanced to a treatment site. In one embodiment, the catheter is advanced to the treatment over a guidewire. At the treatment site, retractable drug delivery device 30 is positioned across the lesion to be treated (Block 630). In one embodiment, retractable drug delivery device 30 and/or distal end of catheter 20 may include radiopaque markers or a radiopaque coating to aid in the visualization and placement of retractable drug delivery device 30 at the treatment site.

Once the retractable drug delivery device 30 is in position, the retractable drug delivery device 30 is deployed (Block 640). In one embodiment, the retractable drug delivery device 30 may be deployed by retracting sheath 40 in a proximal direction to expose and deploy retractable drug delivery device 30. In another embodiment, inner member is advanced in a distal direction to expose and deploy retractable drug delivery device 30. At Block 650 therapeutic agent coating, coated on scaffold struts 62 or membrane 515 contacts the vessel wall and transfers at least a portion of the therapeutic agent to the vessel wall in a therapeutically effective dose.

The deployed scaffold 32 or scaffold with membrane 515 is then covered with sheath 40 upon completion of the delivery of the therapeutic agent (Block 660). Sheath 40, 540 covers device 30 by either advancing sheath in a distal direction to cover retractable drug delivery device 30 or retracting inner member 25, 525 in a proximal direction to draw retractable drug delivery device 30 into sheath 40. The catheter is then withdrawn from the body (Block 670). Method 600 ends at 680.

While the invention has been described with reference to particular embodiments, it will be understood by one skilled in the art that variations and modifications may be made in form and detail without departing from the spirit and scope of the invention.

The invention claimed is:

1. A system for treating a vascular condition, the system comprising:
   a catheter including an inner member and an outer member, the outer member being concentrically arranged and slideably disposed about the inner member;
   a retractable drug delivery device disposed around a distal end of the inner member extending through the retractable drug delivery device, the retractable drug delivery device comprising a plurality of scaffold struts and a plurality of transition struts extending from the plurality of scaffold struts, wherein the scaffold struts of the retractable drug delivery are configured to expand radially from the inner member forming an open passageway wherein the distal end of the scaffold struts are unattached to the inner member;
   an attachment, wherein proximal ends of the plurality of transition struts are secured to the attachment and wherein the attachment is formed integrally with the inner member;
   a coating disposed on at least a portion of an outer surface of the retractable drug delivery device; and in
   at least one therapeutic agent within the coating;
   wherein the inner member and the outer member are operable to collapse the retractable drug delivery device from an expanded configuration to a compressed configuration about the inner member within the outer member when the inner member is moved slideably relative to the outer member.

2. The system of claim 1 wherein the transition struts further comprise an arcuate portion.

3. The system of claim 1 wherein the plurality of scaffold struts and the plurality of transition struts comprise a self-expanding material.

4. The system of claim 1 wherein the retractable drug delivery device further comprises a membrane, the membrane having an outer surface for receiving the coating.

5. The system of claim 1 wherein the outer member further comprises a sheath disposed at a distal end of the outer member and covering the retractable drug delivery device when in a delivery configuration.

6. The system of claim 5 wherein the sheath includes a reinforcing material.

7. The system of claim 6 wherein the reinforcing material comprises a metallic material, a polymeric material and combinations thereof.

8. The system of claim 6 wherein the reinforcing material comprises one of a group consisting of a plurality of braided filaments, a plurality of woven filaments, a coil and a helical coil.

9. The system of claim 8 wherein the reinforcing material is disposed between a first polymeric layer and a second polymeric layer.

10. The system of claim 1 wherein the at least one therapeutic agent is selected from a group consisting of anticoagulants, antiinflammatories, fibrinolytics, antiproliferatives, antibiotics, therapeutic proteins, recombinant DNA products, bioactive agents, diagnostic agents, radioactive isotopes, and radiopaque substances.

* * * * *